US005683719A

United States Patent [19]
Newton

[11] Patent Number: 5,683,719
[45] Date of Patent: Nov. 4, 1997

[54] CONTROLLED RELEASE COMPOSITIONS

[75] Inventor: John Michael Newton, London, England

[73] Assignee: British Technology Group Limited, London, England

[21] Appl. No.: 444,054

[22] Filed: May 18, 1995

Related U.S. Application Data

[63] Continuation of Ser. No. 64,122, filed as PCT/GB91/02057, Nov. 21, 1991, abandoned.

[30] Foreign Application Priority Data

Nov. 22, 1990 [GB] United Kingdom ............... 9025372

[51] Int. Cl.$^6$ ............................................. A61K 9/28
[52] U.S. Cl. ..................... 424/474; 424/432; 424/486; 424/489
[58] Field of Search ................................. 424/474, 486, 424/489, 432

[56] References Cited

U.S. PATENT DOCUMENTS

| | | |
|---|---|---|
| 4,673,565 | 6/1987 | Di Luccio et al. . |
| 4,720,384 | 1/1988 | Di Luccio et al. . |
| 4,888,074 | 12/1989 | Pocknell .................................. 424/432 |

FOREIGN PATENT DOCUMENTS

| | | |
|---|---|---|
| 0 249 949 | 12/1987 | European Pat. Off. . |
| 2 170 104 | 7/1986 | United Kingdom . |
| 2 190 287 | 11/1987 | United Kingdom . |

*Primary Examiner*—John Cooney
*Attorney, Agent, or Firm*—Nixon & Vanderhye

[57] ABSTRACT

A controlled release composition comprising an extruded core of active material and excipients, said core being coated in a water insoluble coating. Preferably the core comprises a pharmaceutically acceptable active ingredient together with microcrystalline cellulose, a clay such as kaolin and a binder such as poly(vinyl-pyrrolidine).

30 Claims, 4 Drawing Sheets

CONTROLLED RELEASE COMPOSITIONS

This is a Rule 62 continuation of application Ser. No. 08/064,122, filed as PCT/GB91/02057, Nov. 21, 1991, now abandoned.

BACKGROUND OF THE INVENTION

This invention relates to extruded controlled release compositions.

The majority of solid oral dosage forms used in the pharmaceutical industry are produced by the compression of powders or granulated powders. The extrusion of wet powder masses has been utilised as a preliminary step in forming the granulate into a useful dosage form but in these cases the extrudate must be subjected to a further processing step. The manufacture of useful dosage forms as the direct product of an extrusion process remains a desirable objective in the art.

DESCRIPTION OF THE INVENTION

We have discovered that a wet mixture of an active material and excipient can be extruded to produce an extruded core having a smooth surface, which when coated in a water insoluble coating will retain its structural integrity upon exposure to an aqueous medium. The coated extruded compositions provide a controlled release of active material, i.e. when exposed to an aqueous medium the active is released into that medium over a prolonged period. Such coated extruded cores are believed to be novel and thus, from one aspect this invention provides a controlled release composition comprising an extruded core of active material and excipients, said core being coated in a water insoluble coating.

The present invention is of broad applicability in the formulation of active substances, particularly biologically active substances. Examples of classes of biologically active materials which may be incorporated in the compositions of the invention include pharmaceuticals, bacteriostats, viruscides, insecticides, herbicides, larvicides, fungicides, algaecides and nematocides. The compositions of this invention find wide application in medicine including veterinary medicine and in horticulture and agriculture as well as outside these areas. The area of particular interest is that of pharmaceutical dosage forms for human or animal use. The preferred compositions of this invention comprise excipients which are pharmacologically acceptable and the invention will be described with particular reference to those preferred embodiments. It will be appreciated that in relation to other embodiments, the use of other materials as excipients may be possible or even preferred.

The wet powder comprising the active and the excipient and also any additional components must be one which is capable of being extruded to form a coherent extrudate. The extrudate preferably has a smooth surface at least on its exterior faces. The composition of the wet mass may need to be adjusted in order to facilitate the production of such preferred extrudates. The nature of the extrudate varies with the proportions of the components of the wet mass and the nature of those components. For any particular active material the nature of and proportions of the remaining components of the wet mass can be adjusted until an acceptable extrudate is formed. Preferably the excipient comprises microcrystalline cellulose. Microcrystalline cellulose materials useful in the compositions of this invention include all those pharmacologically acceptable non-dispersable cellulose derivatives which are known to be useful in the art of tablet formation from wet powder granulates. Examples include all those products sold under the Trade Marks AVICEL and EMCOCEL by the FMC Corporation and Forum Chemicals respectively.

Furthermore, the excipients may include a clay. Clays useful in the compositions of this invention include all those pharmacologically acceptable clays known in the art particularly the kaolinites, montmorillonites, bentonites and attapulgites. The preferred clays are kaolin and bentonite.

Preferred excipients comprise from 25–75% by weight microcrystalline cellulose and from 75–25% by weight of clay. Preferably the proportion of microcrystalline cellulose (hereinafter for convenience termed "MCC") to clay approximately equal, i.e. the ratio of the weight of MCC to clay is preferably within the range 1:1±20% and more preferably 1:1±5%.

Certain grades of commercially available materials sold as microcrystalline cellulose contain minor proportions of other ingredients, e.g. other cellulose derivatives such as carboxymethyl cellulose. Such materials are useful in the compositions of this invention.

The compositions of the present invention preferably comprise at least one pharmaceutically active material.

This material should be one which is not susceptible to significant degredation under the conditions employed to extrude the wet mass. The pharmaceutically active compounds which may usefully be incorporated into the compositions of this invention include all those which may be formulated as tablets by a wet granulation process. The range of active compounds is thereby a wide one and indeed any active which is not significantly degraded by exposure to an aqueous environment in the form of the wet powder mixture or by the conditions employed during the extrusion process or in processing the extrudate especially in drying it may be utilised. Examples of active materials which may be utilised include $\beta$ blockers such as atenolol and metoprolol; calcium antagonists such as nifedipine and nitrendipine, ACE inhibitors such as enalapril and captopril, $\beta_2$ agonists such as salbutamol and terbutaline, hormones, for example androgenic, estrogenic and progestational hormones, notably steroids such as oestradiol, sympathomimetic agents, hypoglycaemic agents, contraceptives, nutritional agents, peptides and proteins, nitrates such as isorbide dinitrate, mononitrate and GTN; xanthines such as theophylline; NSAID's such as piroxicam and dtclofenac; benzodiazepines such as triazolam and zopiclone; $\alpha$ blockers such as prazosine and alfuzosine; antivirals such as acyclovir, zidovudine and ampligen, cephalosporins such as cefaclor, antispasmodics such as alverine and saltcylates such as 5 amino salicyclic acid, preparations containing analgesics, for example asprin. Mixtures of active substances may be incoporated into the controlled release device.

The proportion of the pharmaceutically active material which is incorporated may vary between wide limits, say from 1.0 to 20% by weight of the total weight of the excipients, up to as much as 50%, or even 80% by weight in the case of actives which do not adversely affect the nature of the extruded core. In particular, the amount of active which may be incorporated may detract from the ability of the core to retain its structural integrity in an aqueous medium. The maximum quantity of any particular active which can be incorporated may be determined empirically.

The wet mass which is to be extruded to form the core of the compositions of this invention will normally be wetted with water. However, it may be wetted with non-aqueous liquids and this may be preferable for example where the active material is water sensitive or where the active is not soluble in water to a degree which facilitates the formation of the extrudate. A variety of non-aqueous solvents may be utilised and in the preferred embodiments these will be pharmacologically acceptable organic solvents. Examples of non-aqueous solvents which may be used include the lower alcohols especially ethanol and hydrocarbons such as mineral oils and paraffin oils. Where these non-aqueous solvents are utilised, the excipient must be organophilic. A preferred group of organophilic excipients are the clays as described above.

The amount of liquid which Is added to the dry components will be such as to render the matter mass susceptible to extrusion. The amount may vary within wide limits but in general quantities of from 20 or 40% to 60% of the total weight of the dry ingredients may be utilised.

Particular examples of water sensitive drugs include acetyl salicylic acid (asprin), procaine, cocaine, physostigmine, tetracaine, methyl dopate, dtbukucaine, ergotamine benzyl-penicillin sodium, chloramphenicol, nitrozepan, chlordiaze-poxide, penicillins and cephalosporins. Other active materials which may advantageously be used in the processes of this invention include water soluble vitamins, bronchodilators such as salbutamol, highly deliquescent compounds such as potassium chloride. Further water-sensitive active materials include water soluble materials that form highly viscous solutions when dissolved in water. Examples of such materials are the sugars, including sucrose, dextrose, fructose and hydrophobic polymers.

In a preferred embodiment the excipient includes a water soluble polymeric binder such as poly(vinylpyrrolidine (PVP), gelatin, acacia or starch. Such a binder is conveniently incorporated by utilising an aqueous solution thereof to wet the dry ingredients. Generally the use of a dilute solution containing from 0.5% to 10% by weight of binder will be suitable. The use of such a binder exerts an advantageous effect upon the mechanical properties of the extruded core.

The dry powder mixtures of this invention may comprise a minor proportion generally not more than 20% by weight and preferably not more than 10% by weight of other conventional powder excipients. The weight of such additional excipients may be equal to but will not normally exceed the combined weight of the MCC and the clay. Examples of such excipients include calcium carbonate, barium sulphate, lactose, starch and the carboxymethylcelluloses etc. The presence of these additional excipients may exert a deleterious effect upon the properties of the extruded product and the proportions of such excipients which are employed should preferably be adjusted so as to keep these deleterious effects within acceptable limits.

The wet mass is formed into the core of the controlled release dosage form by extrusion through a die. The nature of the die will influence the shape and hence the release characteristics of the extruded core. For example, the active wet mass can be extruded through circular, elliptical or annular dies. Thus, the extruded cores may be circular or annular in cross-section, i.e. rods or hollow tubes. Typically such rods or tubes will have an external diameter of from 1 mm to 20 mm, preferably from 2 mm to 8 mm, and in the case of the hollow tubes an internal diameter of from ½ mm to 10 mm. The extruded lengths of material may be cut into appropriate lengths to produce the dosage forms. The geometrical dimensions of such rods and tubes will, of course, be dependent on the use of the rod or tube. Thus, for use in humans the tubes or rods will be of a size suitable for swallowing, whereas for animal use they may be correspondingly larger. Suitable lengths for tubes or rods for human use is from 5 to 20 mm.

The extrusion process may be carried out using equipment and techniques which are known in the art of extrusion processing. Examples of extrusion equipment which may be utilised include end plate extruders, screen extruders, rotary cylinder extruders, rotary gear extruders and ram extruders. The operating parameters of the extruder will be adjusted so as to optimise the properties of the extrudate in accordance with techniques which are familiar to those skilled in the art of extrusion. Thus, for example the rate and temperature of the materials to be extruded and the pressure to which they are subjected may need to be adjusted in order to produce a useful extrudate.

By appropriate adjustment to the force applied to cause extrusion and if necessary to the composition of the mixture, it should be possible to obtain an extradate under steady-state flow conditions which has an acceptably smooth surface. The speed of extrusion may vary but those formulations which can be extruded relatively rapidly say at least 5 m $min^{-1}$ are preferred for present use.

The extrudates are normally dried prior to their being incorporated into the controlled release devices of the present invention. However, it is possible to incorporate them into such a device prior to their being dried as hereinafter described.

In order that the extrudates retain their structural integrity during the period over which the active material is to be released, it is necessary that they be coated with a water insoluble material. Such a coating may extend over the entire surface of the extrudate provided that it is sufficiently water permeable to facilitate the release of the active material. However, usually the coating will extend over the majority of the surface area of the extrudate leaving an area uncoated or coated with a permeable material through which the active material is released. Where a portion of the surface of the extrudate is uncoated at least some of the active may be released by erosion of the core. However, in the preferred embodiments, the amount of erosion will be relatively small and certainly less than will compromise the integrity of the device. In the case of the rod shaped or other elongated extrudates, the extrudate may conveniently be coated prior to being chopped into smaller pieces. The cut ends of the chopped rods are left uncoated and the active is released wholly or partially through these uncoated areas. In a similar manner the hollow tubes can be coated and chopped to produce dosage forms in which the cut ends and interior surfaces of the tube are uncoated or coated in a permeable material, and release may take place through these areas.

Processes for the production of these controlled release forms are believed to be novel and form a second aspect of this invention. The invention provides a process for the production of a controlled release composition which comprises extruding a wet mass of active material and excipient and coating the extrudate so as to preserve its structural integrity in an aqueous medium.

The extrudates may be and preferably are chopped into pieces prior to drying. The pieces may be subjected to further processing steps. The dry extrudates typically have a density of from 1.5 to 3.0 gm/cc.

The coated extruded cores will retain their structural integrity for a period after ingestion. Both the geometric form and nature of the coating will influence the delayed release characteristics. Thus, cores of a hollow cylindrical form may have their outer exterior surface coated in a water insoluble material and the inner exterior surface uncoated, or coated in a water soluble or water permeable material. In either variation, dissolution of the active material will principally occur from the interior surface and proceed in a controlled manner. The nature and area of application of the coating is such as to retain the structural integrity of the composition, whilst permitting a controlled release of active.

Suitable water insoluble coatings include ethyl cellulose, polymethyl-methacrylate and aqueous dispersions thereof. Suitable permeable coatings include cellulose derivatives such as hydroxypropyl-methylcellulose and methylcellulose. Additionally plasticizers may be included in the coating such as polyethylene glycol (PEG), glycerol and its esters and phthalate esters. Such coatings are known in pharmaceutical technology and thus any comparable coating that will retain the structural integrity of the extruded core may be used.

Furthermore, the invention includes extruded cores that are hollow tubes wherein the hollow centre is filled by a second pharmaceutically acceptable material. Preferably the second pharmaceutically acceptable material is co-extruded with the extruded core. In such a case the interior extruded form may be of the kind of the present invention or of any other extrudable kind.

A cylindrical extruded core of the present invention may be co-extruded with a second pharmaceutically acceptable material such as the core fills the hollow centre of the second active material. In such a case the coating may be applied to the exterior surface of the co-extrudate, or the co-extrudate may act as a coating in itself.

The extruded forms may form the core of a layered tablet. They may be inserted into a capsule either singly or in numbers. Where a number of forms are enclosed in a capsule they may be identical or different. In some applications it may be convenient to co-extrude a coating onto the extruded wet dosage form.

BRIEF DESCRIPTION OF THE DRAWINGS

The invention will now be described in more detail with reference to the accompanying drawings, in which FIGS. 1–8 each show plots of percentage release of drug against time measured in hours.

EXAMPLES

Figure 1:
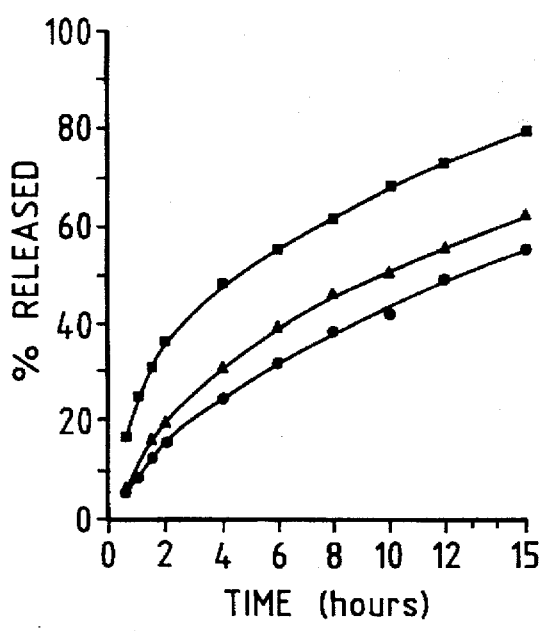

The invention will now be further illustrated by the following examples:

Example 1

Preparation of Extruded Cores

A dry powder mix was formed by introducing the ingredients listed below into a planetary mixer (Kenwood) and mixing for five minutes. The fluid medium, either purified water or a 5% w/v solution of poly(vinyl pyrroltdine) was introduced and the mixing continued for ten minutes. The resulting wet mixture was inserted into the barrel of a ram extruder having a barrel of diameter 2.54 cm fitted with a specially designed annular die. The ram was attached to the cross-head and driven at a rate of 100 mm/min.

Using different annular dies, tubular extruded cores were obtained of different external:internal diameter ratios (E/I). The annular die was replaced by a circular one to produce rods. The tubes and rods were cut to the lengths stated.

The extrudates were dried by being placed in an oven overnight at 55°–60° C. They were cut into lengths 5, 10, 15 and 20 mm and trimmed by scalpel. The permeable coating used comprised PEG4000 20–60% w/w and ethylcellulose (EC) N50 2.5–5% w/v dissolved in equal parts of methylene chloride and methanol. The non-permeable coating comprised N50 (EC) 5% w/v in the methylene chloride methanol solvent. Coating was performed using an Aeromatic AG Stream 1 fluidised bed coater (ACM Machinery, Tadly) and operated under the following optimised conditions in all coating processes:

| | |
|---|---|
| Atomised air pressure | 0.4 bar |
| Feed rate of coating dispersion | 5 G/M |
| Fluidisation air (fan capacity) | 9 units |
| Inlet temperature | 50° C. |
| Drying temperature | 50° C. |
| Drying time | 30 minutes |

The following ingredients in grams were used to prepare tubular extruded cores of theophylline. The percentage theophylline content is given at the bottom of the table.

| Code | R1 | R2 | R3 | R4 |
|---|---|---|---|---|
| Avicel PH 101 | 50 | 50 | 50 | 50 |
| Kaolin light | 50 | 50 | 50 | 50 |
| Calcium carbonate | 90 | 60 | 25 | — |
| PVP (5% w/v in water) | 90 | 90 | 90 | 90 |
| Theophylline (anhydrous) | 10 | 50 | 75 | 100 |
| % Theophylline content | 4.89 | 23.3 | 36.6 | 48.9 |

The following ingredients in grams were used to prepare rods and tubular extruded cores of riboflavin.

| Code | R5 | R6 | R7 | R8 | R9 | R10 | R11 | R12 |
|---|---|---|---|---|---|---|---|---|
| Avicel PH 101 | 25 | 25 | 25 | 25 | 25 | 25 | 25* | 25* |
| Kaolin light | 25 | 25 | 25 | 25 | 25 | 25 | — | — |
| Riboflavin | 5 | 5 | 5 | 5 | 5 | 5 | 5 | 5 |
| PVP (5% w/v in water) | — | 42 | — | 40 | — | 45 | — | — |
| Barium sulphate | 45 | 45 | — | — | — | — | 70 | 70 |
| Lactose | — | — | 45 | 45 | — | — | — | 40 |
| Calcium carbonate | — | — | — | — | 45 | 45 | — | — |
| Water | 36 | — | 35 | — | 40 | — | 38 | — |

*Avicel PH 101 replaced by Avicel PH 581, a grade of microcrystalline cellulose which contains sodium carboxymethyl cellulose.

Example 2

Controlled Release by Extruded Cores
Dissolution Study of Film Coated Cores

A. The in-vitro theophylline release of coated tubular extrudate was determined using the paddle unit (method 2) of USPXX1 dissolution test apparatus (model PTWS, Pharma Test Apparatebau, W. Germany). All these tests were conducted in 900 ml of dissolution medium maintained at 37.0°±0.5° C. with paddle. rotation speed of 100 RPM. Sample of 3 ml volume were withdrawn at various predetermined time intervals using an automated sampler (Pharma Test Apparatebau Type PTFC1, W. Germany). The drug concentration of the samples was determined by direct measurement of the UV absorbance at 272 nm using a Perkin Elmer 554 UV-Vis spectrophotometer after appropriate dilution if high drug concentration were used. The tubes were resting in horizontal position on the bottom of the dissolution vessels during the dissolution tests. Each of the samples below were incubated in this system under the conditions stated. In all Figures the ordinate shows % release of drug and the abscissa time in hours.

1. Theophylline tubes: Permeable external surface coat, no internal coating. Core codes: R2 to R4 <E/I=8/4, length 15 mm) Samples were taken over a period of 18 hours. FIG. 1 shows a controlled pattern of release over this time. R2 identified by (■), R3 (▲) and R4 (●).

Figure 2:
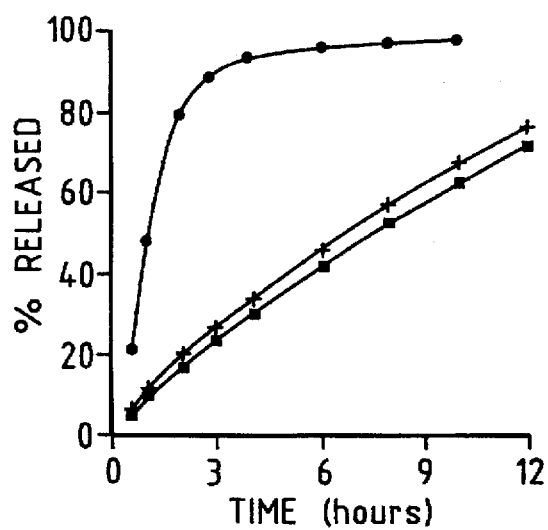

2. Theophylline tubes: Impermeable external coat, no internal coat. Core codes: R1 (E/I=8/4, length 15 mm). The dissolution medium was replaced by (a) phosphate buffer (■), (b) 0.1N HCl (●), (c) distilled water (+). FIG. 2 shows the release profile over a 15 hour period.

Figure 3:
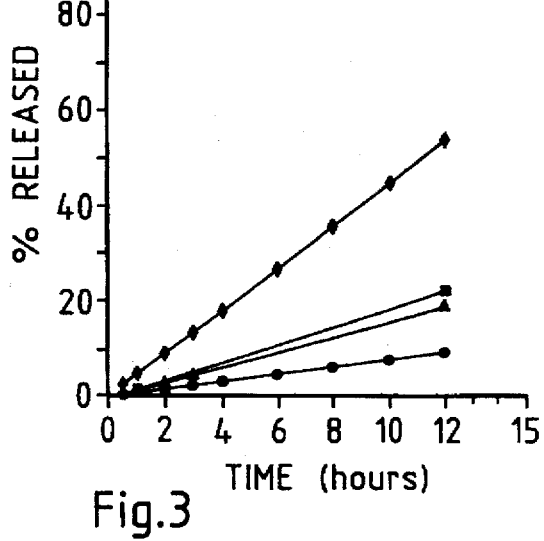
Figure 4:
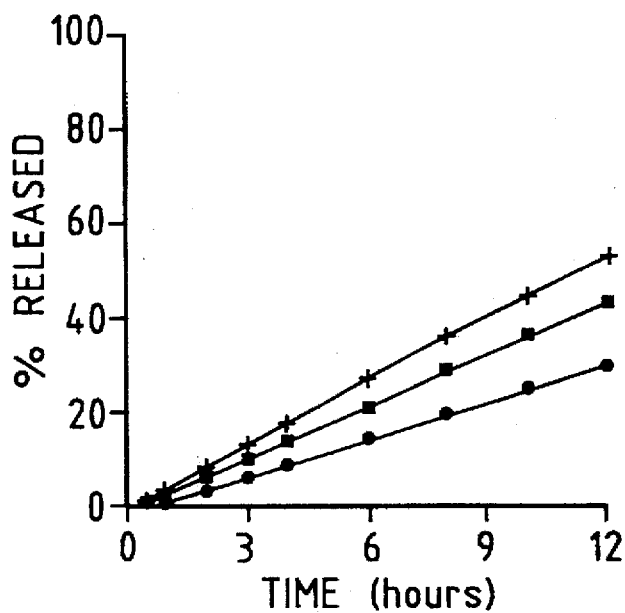

3. Theophylline tubes: External and internal permeable coating. Core codes: R1 to R4 (E/I=8/4, length 5 mm). FIG. 3 shows the release profile over 15 hours (R1 ♦, R2 ■, R3 ▲, R4 ●). FIG. 4 shows R1 in different dissolution media (a) phosphate buffer (■), (b) 0.1N HCl (●), (c) distilled water (+).

Figure 5:
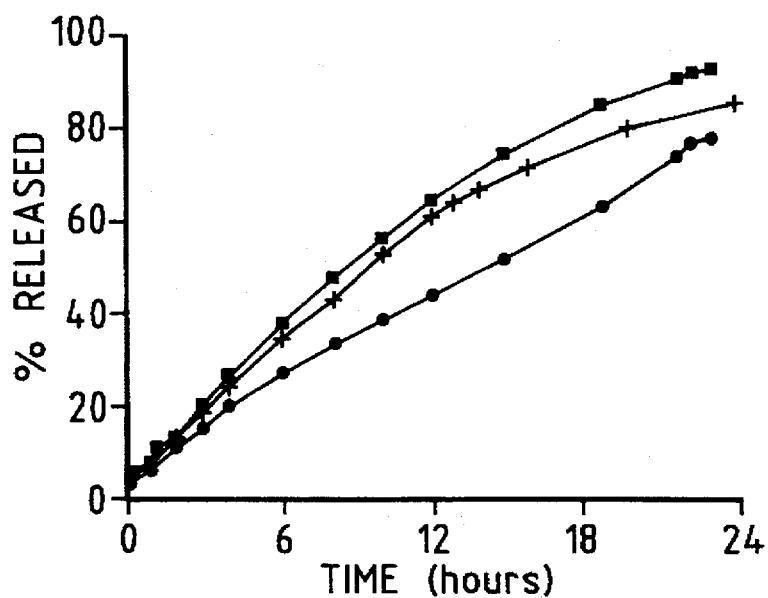

4. Theophylline tubes: Permeable external coat, no internal coat. Core code: R1 (E/I=4/2, length 10 mm). FIG. 5 shows the release profile over 15 hours, in the different dissolution media as described above (a), (b) and (c).

Figure 6:
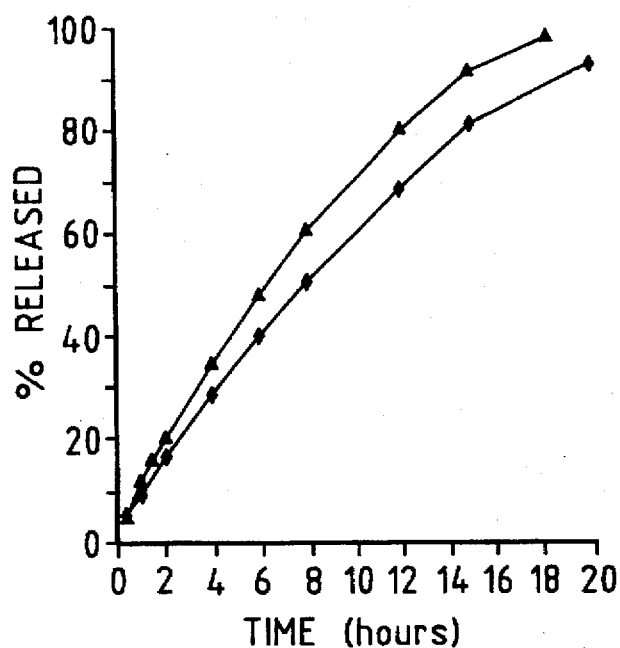

5. Theophylline tubes: Permeable external coat, no internal coat. Core code: R1 (E/I=8/4, length 15 mm). FIG. 6 shows the effect of a 2.5% (▲) and 3.19% (♦) coating on these tubes. (% coating taken as the % by weight of the coated tube).

Figure 7:
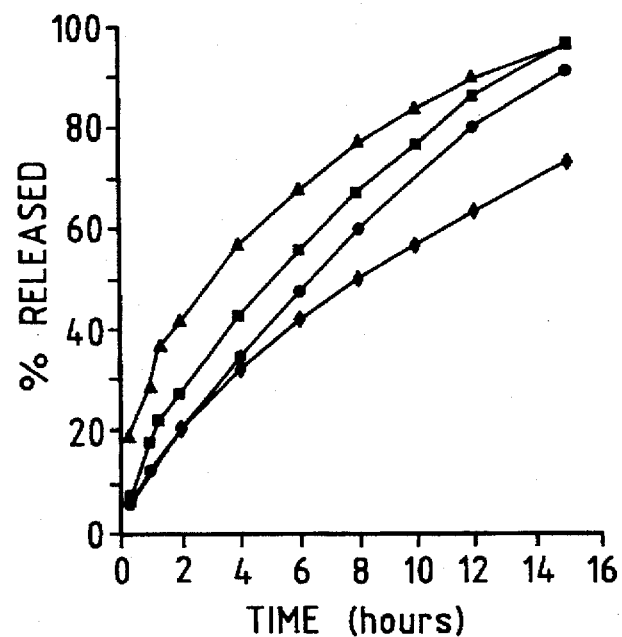

6. Theophylline tubes: Impermeable external coat, no internal coat. Core code: R1 (E/I=8/4). FIG. 7 shows R1 tubes of length 5 mm (■), 10 mm (▲), 15 mm (●) and 20 mm (♦).

Figure 8:
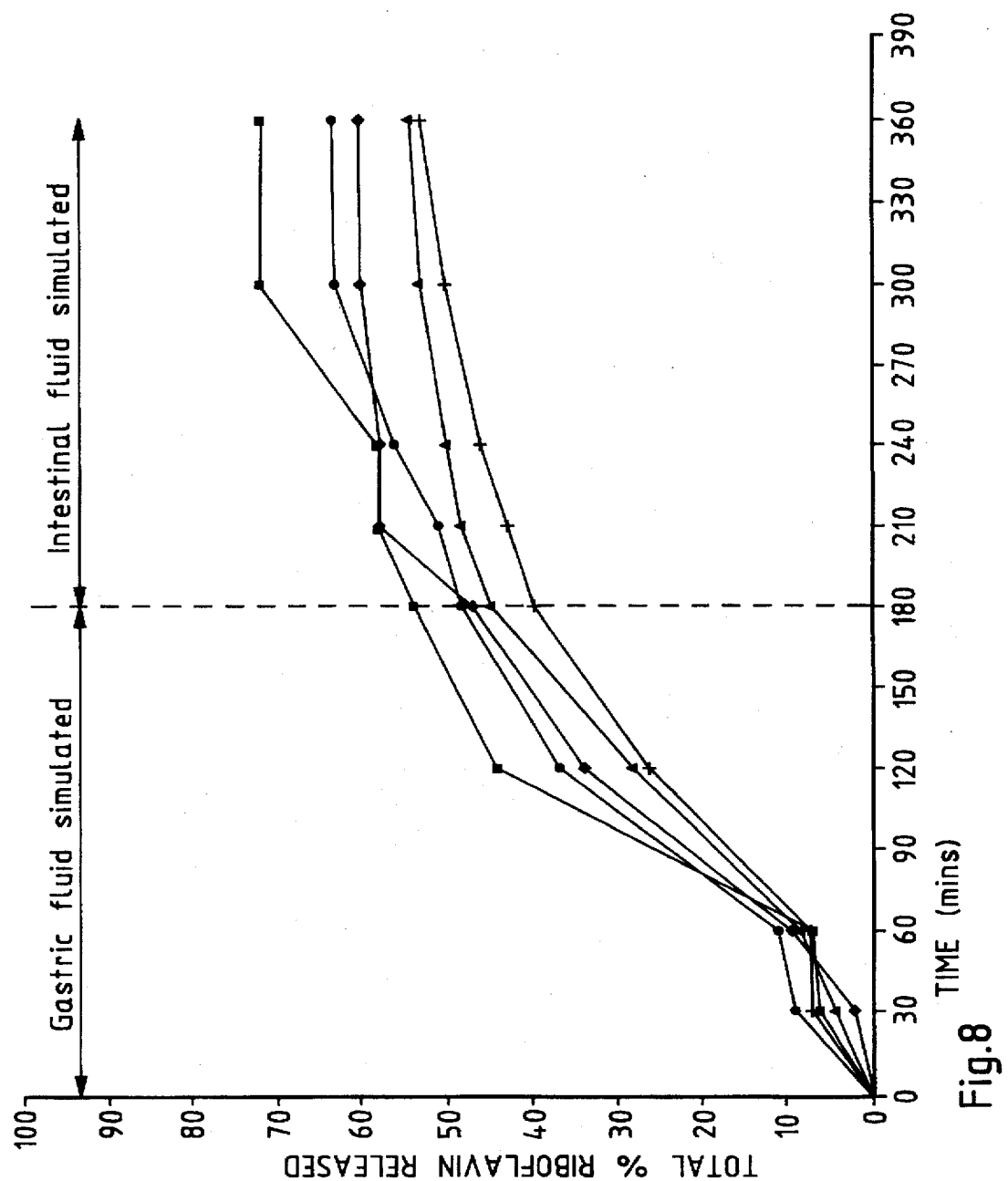

B. The in-vitro release of riboflavin containing extruded tubes and rods was determined using a simulated stomach/intestine model. This model was the paddle unit as described above. The extruded cores are exposed to a simulated gastric fluid (pepsin in 0.1N HCl) for 3 hours, followed by 3 hours in simulated intestinal fluid (pancreatin in 0.2M phosphate buffer). In FIG. 8 the ordinate shows % riboflavin released and the abscissa time in hours.

1. Riboflavin rods (diameter 5 mm) and tubes (external diameter 3 mm, internal diameter 2 mm). All length 15 mm: Coating ECN50, PEG-70%, diethylphthalate 20%. Core codes: R8 (■), R6 (+), R10 (●), all tubes. R8 (♦) and R6 (▲), rods. FIG. 8 shows the release profile over 6 hours. The cores are identified as shown above.

I claim:

1. A controlled release composition in the form of an extruded rod or tube of active material and microcrystalline cellulose and clay excipients, said rod or tube being of at least 2 mm external diameter and being coated with a material having solubility in water such that dissolution of active material proceeds in a controlled manner in aqueous medium and the coated rod or tube retains its structural integrity during the period over which the active material is to be released.

2. A controlled release composition according to claim 1, wherein the active, material is a pharmaceutical.

3. A composition according to claim 1, wherein the clay is selected from the group consisting of kaolinates, montmorillonates, bentonites and attapulgites.

4. A composition according to claim 1, wherein the clay is selected from the group consisting of kaolin and bentonite.

5. A composition according to claim 1, wherein the excipient comprises from 25–75% by weight of microcrystalline cellulose and from 75-25% by weight of a clay.

6. A composition according to claim 5, wherein the ratio of the weight of microcrystalline cellulose to the weight of clay is within the range 1:1±20%.

7. A composition according to claim 1, wherein the active material comprises from 1.0 to 80% by weight of the weight of the total weight of excipient.

8. A composition according to claim 1, wherein the composition includes a binder selected from the group consisting of poly(vinylpyrrolidine), acacia, gelatine and starch.

9. A composition according to claim 8, wherein the binder is poly(vinylpyrrolidine).

10. A composition according to claim 1, wherein the excipient further includes any of the ingredients selected from the group consisting of calcium carbonate, barium sulphate, lactose, starch and carboxymethyl cellulose.

11. A composition according to claim 1 in the form of a tube.

12. A composition according to claim 11, wherein the tube has an annular cross section.

13. A composition according to claim 1, wherein the rod or tube has an external diameter of from 2 mm to 8 mm.

14. A composition according to claim 12, wherein the tube has an internal diameter of from 1 mm to 4 mm.

15. A composition according to claim 1, wherein the rod or tube is from 5 to 20 mm in length.

16. A composition according to claim 1, wherein the majority of the surface of the rod or tube is coated with said material having solubility in water such that the coated rod or tube retains its structural integrity during the period over Which the active, material is to be released.

17. A composition according to claim 1, wherein at least a portion of the surface of the rod or tube is coated with a permeable material.

18. A composition according to claim 17, wherein the entire surface of the rod or tube is coated with a permeable material.

19. A process for the preparation of a controlled release composition in the form of a rod or tube, said method comprising the steps of:

extruding a wet mass comprising active material and microcrystalline cellulose and clay excipients through a die to form a rod or tube of at least 2 mm external diameter; and coating the rod or tube with a material having solubility in water such that dissolution of active material from the rod or tube proceeds in a controlled manner in aqueous medium and the coated rod or tube retains its structural integrity during the period over which the active material is to be released.

20. A process according to claim 19, wherein the die is circular.

21. A process according to claim 19, wherein the die is annular.

22. A process according to claim 19, wherein the rod or tube is dried and subsequently coated.

23. A process according to claim 22, wherein the dried rod or tube is coated with a coating of a material having solubility in water such that the coated rod or tube retains its structural integrity during the period over which the active material is to be released.

24. A process according to claim 21, wherein the outer exterior surface of the tube is coated with a coating of a material having solubility in water such that the coated rod or tube retains its structural integrity during the period over which the active material is to be released.

25. A process according to claim 21, wherein the outer exterior surface of the tube is coated with a water insoluble coating and the inner surface is coated with a water permeable coating.

26. A process according to claim 21, wherein the entire surface of the tube is coated with a permeable material.

27. A controlled release composition in the form of an extruded rod or tube of active material and microcrystalline cellulose and clay excipients, said rod or tube being coated with a material having solubility in water such that dissolution of active material proceeds in a controlled manner in aqueous medium and the coated rod or tube retains its structural integrity during the period over which the active material is to be released, wherein the release of the active material is at a constant rate over a prolonged period.

28. A process as claimed in claim 27, wherein the prolonged period includes the period from 2 to 12 hours in contact with the aqueous medium.

29. A process for the preparation of a controlled release composition in the fore of a rod or tube, wherein a wet mass comprising active material and microcrystalline cellulose and clay excipients is extruded through a die to fore a rod or tube and the rod or tube is coated with a material having solubility in water such that dissolution of active material from the rod or tube proceeds in a controlled manner in aqueous medium and the coated rod or tube retains its structural integrity during the period over which the active material is to be released, wherein the release of the active material is at a constant rate over a prolonged period.

30. A process as claimed in claim 27, wherein the prolonged period includes the period from 2 to 12 hours in contact with the aqueous medium.

* * * * *